United States Patent [19]

Murdock et al.

[11] Patent Number: 4,526,788
[45] Date of Patent: Jul. 2, 1985

[54] POLYMERIC[[(OXAZOLIDINYL)ALKYL]AMINO]ANTHRAQUINONES

[75] Inventors: Keith C. Murdock, Pearl River, N.Y.; Richard L. Webb, Darien, Conn.

[73] Assignee: American Cyanamid Company, Stamford, Conn.

[21] Appl. No.: 476,901

[22] Filed: Mar. 18, 1983

[51] Int. Cl.$^3$ .................. C07D 263/06; A61K 31/42
[52] U.S. Cl. .................................. 514/374; 548/215; 528/125; 528/126; 528/128; 528/224; 528/227
[58] Field of Search ................ 548/215; 424/272; 528/125, 126, 128, 227

[56] References Cited

U.S. PATENT DOCUMENTS

| | | | |
|---|---|---|---|
| 2,865,925 | 12/1958 | Bolen | 548/215 |
| 3,334,100 | 8/1967 | Zenitz | 548/215 |
| 4,275,010 | 6/1981 | Murdock | 260/380 |
| 4,410,524 | 10/1983 | Murdock | 548/215 |

Primary Examiner—Donald G. Daus
Assistant Examiner—S. A. Gibson
Attorney, Agent, or Firm—Edward A. Conroy, Jr.

[57] ABSTRACT

This disclosure describes novel polymeric 1,4-bis-[(1,3-oxazolidin-3-yl)alkylamino]anthraquinones prepared by condensation of 1,4-bis-[(2-hydroxyalkylamino)alkylamino]anthraquinones with dialdehydes which are useful as anti-cancer agents.

7 Claims, No Drawings

POLYMERIC[[(OXAZOLIDINYL)ALKYL-]AMINO]ANTHRAQUINONES

BRIEF SUMMARY OF THE INVENTION

This invention relates to new organic compounds and, more particularly, is concerned with novel polymeric 1,4-bis-[(1,3-oxazolidin-3-yl)alkylamino]anthraquinones which may be represented by the following structural formula:

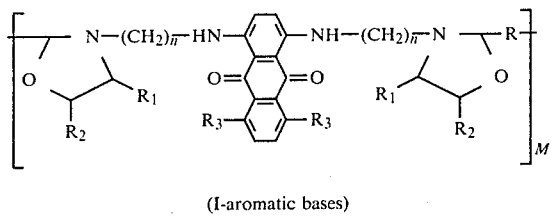

(I-aromatic bases)

wherein n is 2, 3 or 4; $R_1$ is hydrogen or methyl; $R_2$ is hydrogen or methyl; $R_3$ is hydrogen or hydroxy; R is $-(CH_2)_p-$ wherein p is zero, 1, 2, 3 or 4, ortho-phenylene, meta-phenylene or para-phenylene; and M is 2-1000, preferably 2-100.

Also included within the purview of the present invention are the leuco bases and tautomers thereof which may be represented by the following structural formulae:

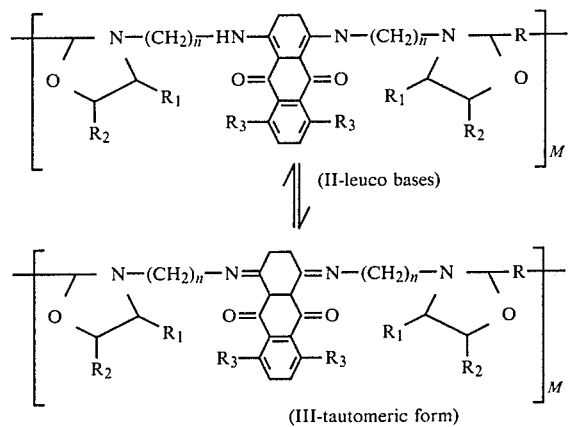

wherein n, R, $R_1$, $R_2$, $R_3$ and M are as hereinbefore defined.

DETAILED DESCRIPTION OF THE INVENTION

The active compounds of the present invention are obtainable as blue-black crystalline materials having characteristic melting points and absorption spectra and which may be purified by leaching with N,N-dimethylformamide or other solvents.

The active compounds of the present invention may be readily prepared in accordance with the following reaction scheme:

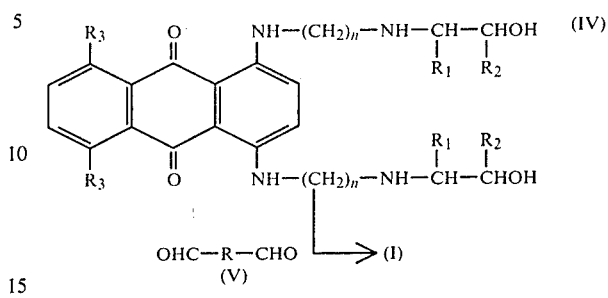

wherein R, $R_1$, $R_2$, $R_3$, n and M are as hereinbefore defined. In accordance with the above reaction scheme, an appropriately substituted symmetrical 1,4-bis[(2-hydroxyalkylamino)alkylamino]anthraquinone (IV) is condensed with a dialdehyde (V) to provide the aromatic bases (I). This reaction is best carried out in an inert solvent such as N,N-dimethylformamide, tetrahydrofuran, dimethylsulfoxide, dioxane and the like at the reflux temperature thereof in the presence of dried 3A molecular sieves for 2-20 hours. Suitable dialdehydes (V) which may be used are glyoxal, malonaldehyde, succinaldehyde, glutaraldehyde, phthalaldehyde, isophthaldehyde and terephthaladehyde. The resulting solid polymer is collected by filtration and washed with dry inert solvent to yield the aromatic bases (I). In like manner, the leuco bases (II) are prepared by condensing the leuco form of (IV) with a dialdehyde (V). The preparation of the starting materials (IV) and the leuco forms thereof is set forth in U.S. Pat. No. 2,051,004, No. 4,051,155, and No. 4,197,249.

The active compounds of the present invention possess the property of inhibiting tumor growth in a mammal.

Lymphocytic Leukemia P388 Test

The animals used are $BDF_1$ mice all of one sex, weighing a minimum of 17 g. and all within a 3 g. weight range. There are 5 or 6 animals per test group. The tumor transplant is by intraperitoneal injection of 0.5 ml. of dilute ascitic fluid containing $10^6$ cells of lymphocytic leukemia P388. The test compounds are administered intraperitoneally on days one, 5 and 9 (relative to tumor inoculation) at various doses. The animals are weighed and survivors are recorded on a regular basis for 30 days. The median survival time and the ratio of survial time for treated (T)/control (C) animals are calculated. The positive control compound is 1,4-dihydroxy-5,8-bis[[2-(2-hydroxyethylamino)ethyl]-amino]anthraquinone dihydrochloride (U.S. Pat. No. 4,197,249; Claim 19) given as a 0.1 mg. or 0.4 mg/kg injection. The results of this test with representative compounds of the present invention appear in Table I. The criterion for efficacy is $T/C \times 100 = \geq 125\%$.

TABLE I

| Compound | Lymphocytic Leukemia P388 Test | | | |
|---|---|---|---|---|
| | Dose mg/kg | Median Survival Time (Days) | T/C × 100 (Percent) | "Cures" 45 Days |
| Poly[5,8-dihydroxy-1,4-anthraquinonylene-iminoethylene[2,2'-bioxazolidine]-3,3'-diylethyleneimino] Fraction (A) | 3.2 | 19.5 | 173 | |
| | 1.6 | 19.0 | 168 | |
| | 0.4 | 14.5 | 128 | |
| Control | | 11.3 | | |

TABLE I-continued

Lymphocytic Leukemia P388 Test

| Compound | Dose mg/kg | Median Survival Time (Days) | T/C × 100 (Percent) | "Cures" 45 Days |
|---|---|---|---|---|
| 1,4-Dihydroxy-5,8-bis[[2-(2-hydroxy-ethylamino)ethyl]amino]anthraquinone dihydrochloride | 0.1 | 17 | 150 | |
| Poly[5,8-dihydroxy-1,4-anthraquinonylene-iminoethylene[2,2'-bioxazolidine]-3,3'-diylethyleneimino] Fraction (B) | 3.2 | 19.0 | 168 | |
| | 1.6 | 19.0 | 168 | |
| | 0.4 | 14.5 | 128 | |
| Control | | 11.3 | | |
| 1,4-Dihydroxy-5,8-bis[[2-(2-hydroxy-ethylamino)ethyl]amino]anthraquinone dihydrochloride | 0.1 | 17 | 150 | |
| Poly[5,8-dihydroxy-1,4-anthraquinonylene-iminoethylene-3,2-oxazolidinediyltri-methylene-2,3-oxazolidinediylethylene-imino] $1^{st}$ Test | 3.2 | 35.5 | 314 | 2/6 |
| | 1.6 | 21.0 | 186 | |
| | 0.4 | 20.5 | 181 | |
| | 0.1 | 18.5 | 164 | |
| | 0.025 | 18.0 | 159 | |
| Control | | 11.3 | | |
| 1,4-Dihydroxy-5,8-bis[[2-(2-hydroxy-ethylamino)ethyl]amino]anthraquinone dihydrochloride | 0.1 | 17 | 150 | |
| Poly[5,8-dihydroxy-1,4-anthraquinonylene-iminoethylene-3,2-oxazolidinediyltri-methylene-2,3-oxazolidinediylethylene-imino] $2^{nd}$ Test | 1.6 | 22 | 186 | |
| | 0.4 | 18.5 | 157 | |
| | 0.1 | 17.5 | 148 | |
| | 0.025 | 16 | 136 | |
| Control | | 11.8 | | |
| 1,4-Dihydroxy-5,8-bis[[2-(2-hydroxy-ethylamino)ethyl]amino]anthraquinone dihydrochloride | 0.1 | 24 | 203 | |
| Poly[5,8-dihydroxy-1,4-anthraquinonylene-iminoethylene-3,2-oxazolidinediyltri-methylene-2,3-oxazolidinediylethylene-imino] 3rd Test | 12.8 | >30 | >268 | |
| | 3.2 | >28 | >250 | |
| | 0.8 | >27 | >241 | |
| | 0.2 | 25.5 | 228 | |
| | 0.05 | 18.5 | 165 | |
| | 0.0125 | 17.0 | 152 | |
| Control | | 11.2 | | |
| 1,4-Dihydroxy-5,8-bis[[2-(2-hydroxy-ethylamino)ethyl]amino]anthraquinone dihydrochloride | 0.4 | 23.5 | 209 | |
| Poly[5,8-dihydroxy-1,4-anthraquinonylene-iminoethylene-3,2-oxazolidinediyl-p-phenylene-2,3-oxazolidinediylethylene-)imino] $1^{st}$ Test | 3.2 | >45 | >398 | 4/6 |
| | 1.6 | 27 | 239 | 1/6 |
| | 0.4 | 24.5 | 217 | |
| | 0.1 | 20.5 | 181 | |
| | 0.025 | 19.5 | 173 | |
| Control | | 11.3 | | |
| 1,4-Dihydroxy-5,8-bis[[2-(2-hydroxy-ethylamino)ethyl]amino]anthraquinone dihydrochloride | 0.4 | 23.5 | 208 | |
| Poly[5,8-dihydroxy-1,4-anthraquinonylene-iminoethylene-3,2-oxazolidinediyl-p-phenylene-2,3-oxazolidinediylethylene-imino] $2^{nd}$ Test | 0.4 | 21.5 | 182 | |
| | 0.1 | 20.0 | 170 | |
| | 0.025 | 15.0 | 127 | |
| Control | | 11.8 | | |
| 1,4-Dihydroxy-5,8-bis[[2-(2-hydroxy-ethylamino)ethyl]amino]anthraquinone dihydrochloride | 0.1 | 24 | 203 | |
| Poly[5,8-dihydroxy-1,4-anthraquinonylene-iminoethylene-3,2-oxazolidinediyl-p-phenylene-2,3-oxazolidinediylethylene-imino] $3^{rd}$ Test | 12.8 | >28.5 | >254 | |
| | 3.2 | 27.5 | 246 | |
| | 0.8 | 25 | 223 | |
| | 0.2 | 18.5 | 165 | |
| | 0.05 | 18.5 | 165 | |
| | 0.0125 | 18.5 | 165 | |
| Control | | 11.2 | | |
| 1,4-Dihydroxy-5,8-bis[[2-(2-hydroxy-ethylamino)ethyl]amino]anthraquinone dihydrochloride | 0.4 | 23.5 | 209 | |

*"Cures" = number of survivors/total at 45 days

Melanotic Melanoma B16

The animals used are $BDF_1$ mice, all of the same sex, weighing a minimum of 17 g. and all within a 3 g. weight range. There are normally 6 animals per test group. A one-gram portion of melanotic melanoma B16 tumor is homogenized in 10 ml. of cold balanced salt solution and a 0.5 ml. aliquot of the homogenate is implanted intraperitoneally into each of the test mice. The test compounds are administered intraperitoneally on days one through nine (relative to tumor inoculation) at various doses. The animals are weighed and survivors are recorded on a regular basis for 60 days. The median survival time and the ratio of survival time for treated (T)/control (C) animals are calculated. The positive control compound is 1,4-dihydroxy-5,8-bis[[2-(2-hydroxyethylamino)ethyl]amino]anthraquinone dihydrochloride (U.S. Pat. No. 4,197,249; Claim 19) given as a 0.1 mg/kg injection. The results of this test with representative compounds of the present invention appear in Table II. The criterion for efficacy is $T/C \times 100 \geqq 125\%$.

TABLE II

| Compound | Dose mg/kg | Median Survival Time (Days) | T/C × 100 (Percent) |
| --- | --- | --- | --- |
| *Melanotic Melanoma B16* | | | |
| Poly[5,8-dihydroxy-1,4-anthraquinonylene-iminoethylene[2,2'-bioxazolidine]-3,3'-diylethyleneimino] Fraction (A) | 6.4 | >52 | >263 |
|  | 1.6 | 41 | 207 |
|  | 0.4 | 26.5 | 134 |
| Control |  | 19.8 |  |
| 1,4-Dihydroxy-5,8-bis[[2-(2-hydroxy-ethylamino)ethyl]amino]anthraquinone dihydrochloride | 0.1 | 42.5 | 215 |
| Poly[5,8-dihydroxy-1,4-anthraquinonylene-iminoethylene[2,2'-bioxazolidine]-3,3'-diylethyleneimino] Fraction (B) | 6.4 | >60 | >303 |
|  | 1.6 | >60 | >303 |
|  | 0.4 | 28.5 | 144 |
|  | 0.1 | 25.0 | 126 |
| Control |  | 19.8 |  |
| 1,4-Dihydroxy-5,8-bis[[2-(2-hydroxy-ethylamino)ethyl]amino]anthraquinone dihydrochloride | 0.1 | 42.5 | 215 |
| Poly[5,8-dihydroxy-1,4-anthraquinonylene-iminoethylene-3,2-oxazolidinediyltri-methylene-2,3-oxazolidinediylethylene-imino] | 3.2 | >54 | >273 |
|  | 0.8 | 44 | >222 |
|  | 0.2 | 30 | 152 |
|  | 0.05 | 27.5 | 139 |
| Control |  | 19.8 |  |
| 1,4-Dihydroxy-5,8-bis[[2-(2-hydroxy-ethylamino)ethyl]amino]anthraquinone dihydrochloride | 0.1 | 42.5 | 215 |
| Poly[5,8-dihydroxy-1,4-anthraquinonylene-iminoethylene-3,2-oxazolidinediyl-p-phenylene-2,3-oxazolidinediylethylene-imino] | 3.2 | >60 | >303 |
|  | 0.8 | >49.5 | >250 |
|  | 0.2 | 25.5 | 129 |
|  | 0.05 | 27.0 | 136 |
| Control |  | 19.8 |  |
| 1,4-Dihydroxy-5,8-bis[[2-(2-hydroxy-ethylamino)ethyl]amino]anthraquinone dihydrochloride | 0.1 | 42.5 | 215 |

Also embraced within the purview of the present invention are therapeutic compositions of matter useful for ameliorating cancer diseases in mammals and containing the polymeric aromatic bases (I) and/or the polymeric leuco bases (II) of the present invention. This aspect of the invention includes the novel compositions of matter and the method of inducing the regression and/or palliation of leukemia and related cancers in mammals when administered in amounts ranging from about one mg. to about 1.2 gm per square meter of body surface area per day. The interrelationship of dosages for animals of various sizes and species and humans (based on mg/m² of surface area) is described by Freireich, E. J., et. al., Quantitative Comparison of Toxicity of Anticancer Agents in Mouse, Rat, Hamster, Dog, Monkey and Man. Cancer Chemother, Rep., 50, No. 4, 219–244, May 1966. A preferred dosage regimen for optimum results would be from about 3 mg/m²/day to about 200 mg/m²/day, and such dosage units are employed that a total of from about 5 mg. to about 360 mg. of the active compound for a subject of 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The active compound may be administered by the intravenous, intramuscular, or subcutaneous routes.

The active compounds may be administered parenterally or intraperitoneally. Solutions or dispersions of the active compound can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy sryringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases it will be preferable to include isotonic agents, for example sugars or sodium chloride. Prolonged absorption of the injectable compositions can be brought about by the use in the compositions of agents delaying absorption, for example aluminum monostearate and gelatin. Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 2 mg. to about 2 g., with from about 5 to about 360 mg. being preferred. Expressed in proportions, the active compound is generally present in from about 2 to about 100 mg/ml of carrier. In the case of compositions containing supplementary active ingredients, the dosages are determined by reference to the usual dose and manner of administration of the said ingredients.

Regression and palliation of cancers are attained, for example, using intraperionteal administration. A single intravenous dosage or repeated daily dosages can be administered. Daily dosages up to about 5 or 10 days are often sufficient. It is also possible to dispense one daily dosage or one dose on alternate or less frequent days. As can be seen from the dosage regimens, the amount of principal active ingredient administered is a sufficient amount to aid regression and palliation of the leukemia or the like, in the absence of excessive deleterious side effects of a cytotoxic nature to the hosts harboring the cancer. As used herein, cancer disease means blood malignancies such as leukemia, as well as other solid and non-solid malignancies such as the malanocarcinomas, lung carcinomas, and mammary tumors. By regression and palliation is meant arresting or retarding the growth of the tumor or other manifestation of the disease compared to the course of the disease in the absence of treatment.

This invention will be described in greater detail in conjunction with the following specific examples.

EXAMPLE 1

Poly[5,8-dihydroxy-1,4-anthraquinonyleneiminoethylene[2,2'-bioxazolidine]-3,3'-diylethyleneimino]

A mixture of 30.0 g of 1,4-dihydroxy-5,8-bis[[2-(2-hydroxyethylamino)ethyl]amino]anthraquinone dihydrochloride (prepared as described in Example 24 of U.S. Pat. No. 4,197,249) and 300 ml of methanol was chilled in an ice bath in a Dewar flask. The mixture was saturated with ammonia gas and was allowed to stand at 0° C. for one hour with the continuous slow addition of ammonia gas and with periodic stirring. The solid was collected by filtration and washed by slurrying with five 150 ml portions of methanol saturated with ammonia gas to give 22.9 g of 1,4-dihydroxy-5,8-bis[[2-(2-hydroxyethylamino)ethyl]amino]anthraquinone as blue-black micro rods, mp 175°–178° C.

A 500 ml, 3-necked flask was fitted with a vacuum addition funnel plugged with glass wool at the bottom. A 30.0 g amount of 3A molecular sieves (activated at 200° C. for 16 hours) was added to the funnel and the funnel was fitted on top with a condenser, U-tube manometer, dry ice trap and vacuum pump. The flask was also fitted with a thermometer and a stopper. A magnetic stirring bar was placed in the flask and the flask was immersed in a silicone oil bath with a magnetic stirrer hot plate as a heat source.

A 3.107 g (7.00 mmole) amount of 1,4-dihydroxy-5,8-bis[[2-(2-hydroxyethylamino)ethyl]amino]anthraquinone free base (prepared as described above) was weighed into a tared vial in a hood. The stopper was removed and the free base was added to the reaction flask with a transfer funnel, using N,N-dimethylformamide. A total of 200 ml of N,N-dimethylformamide was added to the flask. Then the flask was stoppered, stirred and warmed to about 55° C. to achieve solution. The temperature was lowered to about 34° C. and 0.837 ml (7.00 mmole) of 38% glyoxal solution was added dropwise. The flask was restoppered and the system was evacuated to 5–6 mm of mercury and allowed to reflux for 18 hours at a rate of about one to 1.5 ml per minute.

The reaction mixture was allowed to cool, then 11.5 g of 3A molecular sieves (activated as previously described) was added. The mixture was warmed to 40° C. and stirred for several hours, then the temperature of the bath was raised to 98° C. and stirring was continued for 1½ hours. The heat was turned off and the reaction mixture was filtered through a coarse sintered glass funnel with slight vacuum and washed with two 25 ml portions of N,N-dimethylformamide. The filtrate containing a finely divided solid was transferred to a 500 ml round bottomed flask and most of the N,N-dimethylformamide was distilled from the reaction mixture using a Claisen-head distillation apparatus and condenser at a bath temperature not in excess of 62° C. During the distillation a needle-like precipitate formed on the liquid surface along the walls of the flask. The distillation was stopped with about 20–30 ml of liquid remaining in the flask. The cooled mixture of solid and liquid was essentially transferred into an Erlenmeyer flask by spatula and Pasteur pipette using 25–30 ml of N,N-dimethylformamide. Approximately one half of the solvent in this mixture was distilled in vacuo (3–3.5 mm) at a pot temperature of 25°–30° C. Into a receiver maintained in dry ice, leaving 13.5 g of the solid and liquid. The sample was refrigerated at 3° C. for 19 hours. Then the solid was collected in a 15 ml medium porosity sintered glass funnel using vacuum. Th cake was washed with 3 ml then 2 ml of dry, cold N,N-dimethylformamide and was transferred to a tared vial to give Fraction A. The crystallization flask and spatula were rinsed with dry N,N-dimethylformamide and added to the filtrate for concentration at room temperature with magnetic stirring to give a moist residue which was transferred to a tared vial to give Fraction B. Drying in vacuo gave 0.571 g of Fraction A, mp 232°–239° C. and 0.8665 g of Fraction B, mp 206°–211° C.

EXAMPLE 2

Poly[5,8-dihydroxy-1,4-anthraquinonyleneiminoethylene-3,2-oxazolidinediyltrimethylene-2,3-oxazolidinediylethyleneimino]

A 250 ml, 3 necked flask was fitted at the right neck with an appropriate Soxhlet apparatus, the Soxhlet condenser was connected to a U-tube manometer, dry ice trap and vacuum pump. The center neck was fitted with a thermometer and the left neck was stoppered. A Soxhlet thimble containing 35 g of 3A molecular sieves activated at 200° C. for 16 hours) was placed in the Soxhlet apparatus and 70 ml of dried N,N-dimethylformamide was added to the thimble, at which point the solvent was siphoned into the reaction flask, then 50 ml more of N,N-dimethylformamide was added to prevent the flask from later running dry. A magnetic stirring bar was placed in the reaction flask and the flask was immersed in a silicone oil bath with a magnetic stirrer hot plate as a heat source.

A 3.116 g (7.02 mmole) amount of 1,4-dihydroxy-5,8-bis[[2-(2-hydroxyethylamino)ethyl]amino]anthraquinone was weighed into a tared vial in a hood. The stopper was removed and the free base was added with stirring to the reaction flask with a transfer funnel using 2 ml and 3 ml amounts of additional N,N-dimethylformamide for a quantitative transfer. The flask was restoppered, stirring was continued, vacuum was applied and the oil bath was heated. As the bath temperature neared 65° C. and the thimble filled to 90% volume with solvent the vacuum was released and 2.80 g (7.00 mmole) of 25% aqueous glutaraldehyde solution, weighed into a tared vial, was added to the reaction mixture at about ½ drop per second near the edge of the vortex. When the addition was complete the flask was restoppered, vacuum was reapplied (8.5–9 mm) and refluxing was continued for a total of one hour and 55 minutes after the glutaraldehyde addition, at a bath temperature of 49°–65° C. The heat and vacuum were turned off and the reaction flask was allowed to stand at room temperature for 16 hours, leaving a considerable amount of solid on the walls of the reaction flask. The solid was collected by filtration through a 15 ml, medium porosity sintered glass funnel, then was washed twice with 5 ml portions of dry N,N-dimethylformamide to give 8.33 g of a moist cake. The cake was dried to constant weight in vacuo at room temperature to give 3.26 g of the product of the Example as a dark blue powder, mp >350° C.

EXAMPLE 3

Poly[5,8-dihydroxy-1,4-anthraquinonyleneiminoethylene-3,2-oxazolidinediyl-p-phenylene-2,3-oxazolidinediylethyleneimino]

A 12.0 g amount of terephthalaldehyde was recrystallized from one liter of 95° C. deionized water and dried in vacuo at room temperature to yield 9.5 g of purified product.

Using the same apparatus described in Example 2 with the same 3A molecular sieves in the thimble and 30% filled with dried N,N-dimethylformamide, a 40 ml amount of dried N,N-dimethylformamide was added to the 250 ml 3-necked flask. A 3.104 g (6.99 mmole) amount of 1,4-dihydroxy-5,8-bis[[2-(2-hydroxyethylamino)ethyl]amino]-anthraquinone was weighed into a tared vial in a hood. The stopper was removed and the free base was added with magnetic stirring, to the reaction flask with a transfer funnel using 2 ml and 3 ml additional amounts of N,N-dimethylformamide for a quantitative transfer. The flask was restoppered, stirring was continued, vacuum was applied and the oil bath was heated to 50° C. and maintained at that temperature for 30 minutes. A 0.934 g (6.96 mmole) amount of the purified terephthalaldehyde was dissolved in 40 ml of dry N,N-dimethylformamide. The vacuum was turned off and the aldehyde solution was added to the reaction flask at about 4 drops per second. The flask was restoppered and vacuum was restored. The temperature was raised to 58°–59° C. and refluxing was continued for a total of 3 hours and 40 minutes after the terephthalaldehyde addition. The heat was removed and the reaction flask was cooled to 23° C. in water. The resulting solid was collected by filtration through a 15 ml medium porosity sintered glass funnel and washed twice with 5 ml portions of dried N,N-dimethylformamide. The cake was slurried with 10 ml of cold dried N,N-dimethylformamide for one minute, was recollected and washed with another 5 ml of dried N,N-dimethylformamide and was pressed dry to give 9.7 g of a cake. The cake was dried in vacuo to constant weight to give 2.210 g of the desired product as a dark blue powder, mp >350° C.

EXAMPLE 4

Poly[5,8-dihydroxy-1,4-anthraquinonyleneiminoethylene-3,2-oxazolidinediyl(4-chloro-1,2-phenylene)-2,3-oxazolidinediylethyleneimino]

When 4-chlorophthalaldehyde [M. Kerfanto and N. Soyer, bull. Soc. Chim. France, 2966 (1966)] is substituted for terephthalaldehyde in the procedure of Example 3 the desired product is obtained.

EXAMPLE 5

Poly[2,3-dihydro-5,8-dihydroxy-1,4-anthraquinonyleneiminotrimethylene-3,2-oxazolidinediyltrimethylene-2,3-oxazolidinediyltrimethyleneimino]

The apparatus of Example 2 is slightly modified by the insertion of an ebulating tube into the reaction lask. This tube is adjusted to extend below the surface of the reaction mixture and is used to bubble argon gas through the reaction mixture during the heating and refluxing period.

A 7.00 mmole amount of 2,3-dihydro-5,8-dihydroxy-1,4-bis[[3-(2-hydroxyethylamino)propyl]amino]anthraquinone (prepared as described in Example 27 of U.S. Pat. No. 4,197,249) is substituted for 7.02 mmole of 1,4-dihydroxy-5,8-bis[[2-(2-hydroxyethylamino)ethyl]amino]-anthraquinone in the procedure of Example 2 and argon gas is utilized as hereinabove described, to obtain the product of the Example.

EXAMPLE 6

Poly[5,8-dihydroxy-1,4-anthraquinonyleneimino-trimethylene-3,2-oxazolidinediyl-p-phenylene-2,3-oxazolidinediyltrimethyleneimino]

1,4-Dihydroxy-5,8-bis[[3-(2-hydroxyethylamino)-propyl]amino]anthraquinone dihydrochloride (prepared as described in Example 28 of U.S. Pat. No. 4,197,249) is converted to 1,4-dihydroxy-5,8-bis[[3-(2-hydroxyethylamino)propyl]amino]anthraquinone free base using the procedure described in Example 1.

A 7.00 mmole amount of the preceding free base is substituted for 6.99 mmole of 1,4-dihydroxy-5,8-bis[[2-(2-hydroxyethylamino)ethyl]amino]anthraquinone free base in the procedure of Example 3 to give the product of the Example.

EXAMPLE 7

Poly[5,8-dihydroxy-1,4-anthraquinonyleneiminoethylene(5-methyl-3,2-oxazolidinediyl)trimethylene(5-methyl-2,3-oxazolidinediyl)ethyleneimino]

A mixture of 6.0 g of 1,4-dihydroxy-5,8-bis[[2-[(2-hydroxypropyl)amino]ethyl]amino]anthraquinone dihydrochloride (prepared as described in Example 32 of U.S. Pat. No. 4,197,249) and 60 ml of methanol is treated with ammonia gas according to the procedure of Example 1 to give the corresponding free base, 1,4-dihydroxy-5,8-bis[[2-[(2-hydroxypropyl)amino]ethyl]amino]-anthraquinone.

A 7.00 mmole amount of the preceding free base is substituted for 7.02 mmole of 1,4-dihydroxy-5,8-bis[[2-(2-hydroxyethylamino)ethyl]amino]anthraquinone, free base in the procedure of Example 2 to give the desired product.

EXAMPLE 8

Poly[5,8-dihydroxy-1,4-anthrquinonyleneiminoethylene-3,2-oxazolidinediyl(2,5-furandiyl)-2,3-oxazolidinediylethyleneimino]

When furan-2,5-dicarboxaldehyde [A. F. Oleinik and K. Yu. Novitskii, Zhur. Org. Khim., 6, 2632 (1970)] is substituted for terephthalaldehyde in the procedure of Example 3 the product of the Example is obtained.

EXAMPLE 9

Poly[1,4-anthraquinonyleneiminoethylene-3,2-oxazolidinediyltrimethylene-2,3-oxazolidinediylethyleneimino]

When 2.89 g (7.02 mmole) of 1,4-bis[[2-[(2-hydroxyethyl)amino]ethyl]amino]anthraquinone [U.S. Pat. No. 2,051,004 (1936), Koeberle, et al. and U.S. Pat. No. 4,051,155 (1977), R. C. Hoare is substituted for 3.116 g (7.02 mmole) of 1,4-dihydroxy-5,8-bis[[2-(2-hydroxyethylamino)ethyl]amino]anthraquinone in the procedure of Example 2 the desired product is obtained.

EXAMPLE 10

Preparation of Parenteral Suspension

In a solution of 700 ml of propylene glycol and 200 ml of water for injection is suspended 20.0 g of poly[5,8-dihydroxy-1,4-anthraquinonyleneiminoethylene-3,2-oxazolidinediyltrimethylene-2,3-oxazolidinediylethyleneimino] with stirring. After suspension is complete, the volume is made up to 1000 ml with water for injection. The formulation is sterilized, filled into 5.0 ml ampoules each containing 2.0 ml (representing 40 mg of drug) and sealed under nitrogen.

EXAMPLE 11

Preparation of Parenteral Suspension

The active compound in powder form is sterilized by ethylene oxide sterilization. The sterilized powder is aseptically filled into vials in dosage unit form and the vials are sealed. Immediately prior to use the powder is suspended by the addition of a suitable sterile diluent. The resulting suspension may be sonicated if necessary to promote dispersion. (This mode of suspension is advantageous for compounds which might undergo some hydrolysis on long standing in an aqueous medium.)

We claim:

1. A polymer selected from the group consisting of those of the formula:

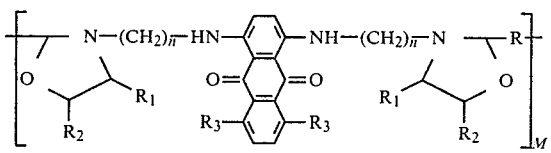

wherein n is 2, 3 or 4; $R_1$ is hydrogen or methyl; $R_2$ is hydrogen or methyl; $R_3$ is hydrogen or hydroxy; R is —$(CH_2)_p$— wherein p is zero, 1, 2, 3 or 4, o-phenylene, m-phenylene or p-phenylene; and M is 2–1000; the leuco bases thereof and the tautomers thereof.

2. The polymer according to claim 1 wherein n is 2, R is zero, $R_1$ and $R_2$ are both hydrogen, and $R_3$ is hydroxy; poly[5,8-dihydroxy-1,4-anthraquinonyleneiminoethylene[2,2'-bioxazolidine]-3,3'-diylethyleneimino].

3. The polymer according to claim 1 wherein n is 2, R is trimethylene, $R_1$ and $R_2$ are both hydrogen, and $R_3$ is hydroxy; poly[5,8-dihydroxy-1,4-anthraquinonyleneiminoethylene-3,2-oxazolidinediyltrimethylene-2,3-oxazolidinediylethyleneimino].

4. The polymer according to claim 1 wherein n is 2, R is p-phenylene, $R_1$ and $R_2$ are both hydrogen, and $R_3$ is hydroxy; poly[5,8-dihydroxy-1,4-anthraquinonyleneiminoethylene-3,2-oxazolidinediyl-p-phenylene-2,3-oxazolidinediylethyleneimino].

5. A pharmaceutical composition is dosage unit form comprising from about one mg./m² to about 1.2 g./m² of body surface area of a polymer of claim 1 in association with a pharmacologically acceptable carrier.

6. The method of inducing regression of leukemia and/or inhibiting tumor growth in a mammal comprising administering to said mammal an effective amount of a composition of claim 5.

7. The process of preparing a polymer of the formula:

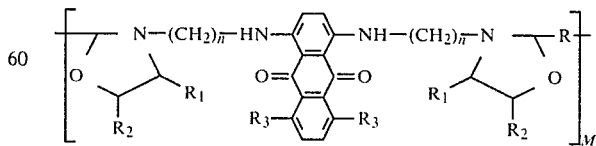

wherein n is 2, 3 or 4; $R_1$ is hydrogen or methyl; $R_2$ is hydrogen or methyl; $R_3$ is hydrogen or hydroxy; R is —$(CH_2)_p$— wherein p is zero, 1, 2, 3 or 4, ortho-phenylene, meta-phenylene or para-phenylene; and M is 2-1000, preferably 2-100; which comprises condensing a compound of the formula:

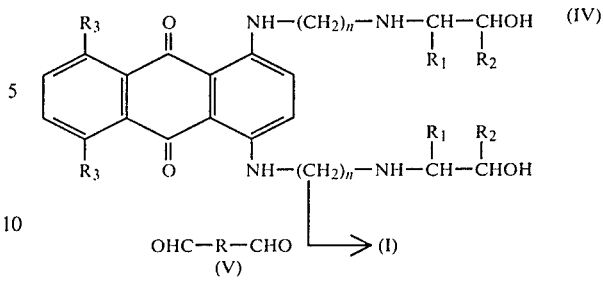

wherein $R_1$, $R_2$, $R_3$ and n are as hereinabove defined with a dialdehyde of the formula: OHC—R—CHO wherein R is as hereinabove defined in an inert solvent at the reflux temperature thereof in the presence of 3A molecular sieves for a period of time sufficient for a substantial degree of condensation to occur.

* * * * *